United States Patent [19]

Baeder et al.

[11] Patent Number: 5,321,009

[45] Date of Patent: Jun. 14, 1994

[54] METHOD OF TREATING DIABETES

[75] Inventors: William L. Baeder, Cranbury; Surendra N. Sehgal, Princeton, both of N.J.; Laurel M. Adams, Durham, N.C.; Thomas J. Caggiano, Morrisville, Pa.

[73] Assignee: American Home Products Corporation, Madison, N.J.

[21] Appl. No.: 792,105

[22] Filed: Nov. 14, 1991

Related U.S. Application Data

[63] Continuation-in-part of Ser. No. 679,706, Apr. 3, 1991, abandoned.

[51] Int. Cl.$^5$ .............................................. C07K 7/40
[52] U.S. Cl. ............................................ 514/4; 514/3; 514/9; 514/291
[58] Field of Search ............................ 514/3, 4, 9, 291

[56] References Cited

U.S. PATENT DOCUMENTS

| | | | |
|---|---|---|---|
| 3,929,992 | 12/1975 | Sehgal et al. | 424/122 |
| 4,362,719 | 12/1982 | Cavazza | 424/128 |
| 5,078,999 | 1/1992 | Warner et al. | 424/122 |
| 5,080,899 | 1/1992 | Sturm et al. | 424/122 |
| 5,118,678 | 6/1992 | Kao et al. | 540/456 |

FOREIGN PATENT DOCUMENTS 0401747 of 0000 European Pat. Off. .

OTHER PUBLICATIONS

Collier et al. CA 113: 224286 vol. 113, 1990.
Eisenbarth, New Eng. J. Med. vol. 314, No. 21 (May 1986) 1360–8.
Kurasawa et al. "Clin. Immunology Path." vol. 57, 274 (1990).
Miyagawa et al. CA 3112 (vol. 114) 1991.
Baeder et al. Abstract, 5th Int'l Conf. Inflamm. Res. Assoc. (Sep. 23, 1990).
Atkinson et al. *Diabetes* vol. 39 (Aug. 1990) pp. 933–937.
Dumont & Melino et al J. Immun. vol. 144 (Feb. 1990) 1418.
Rakel, Editor, Conn's Current Therapy (W. B. Saunders 1989) 482–98.
Dumont & Staruch et al. J. Immun. vol. 144 (Jan. 1990) 251.
J. Pharmacol. Exp. Ther. 241: 1106 (1987).
Metalbolism 32 Supp 1: 69 (1983).
Clin. Invest. Med. 10: 488 (1987).
Diabetologia 29: 244 (1986).
Lancet 120 (Jul. 1986).
Diabetes 37: 1574 (1988).
Science 223: 1362 (1984).
Diabetes Care 13: 776 (1990).
Diabetes 39: 1584 (1990).
Clin. Immunol. Immunopath. 57: 274 (1990).
Diabetologia 33: 503 (1990).
Abst. distributed at Fifth Intern'l Conf. Inflam. Res. Assoc. 121 (Sep. 23, 1990).
Can J. Physiol. Pharmocol. 55, 48 (1977).
FASEB 3,3411 (1989).
Med. Sci. Res. 17: 877 (1989).
Basic & Clin. Immunol. Stites ed., Appleton/Lange, 7th ed. p. 471 (1991).
Am. J. Path. 128: 380 (1987).
Diabetes 40: 715 (1991).
Diabetes 37: 1591 (1988).
Annu. Rev. Med. 41: 497 (1990).
Lancet 845 (Apr. 16, 1988).
Immunol. Today 12: 137 (1990).
J. Immunol. 144: 251 (1990).
J. Immunol. 444: 1418 (1990).
Brayman, K. L., Surgical Forum 42: 405 (1991).
Meiser, B. M., Progress in Immunology 7: 1195 (1989).
Boitard, C., Diabetes/Metabolism Reviews 7: 15 (1991).

*Primary Examiner*—Lester L. Lee
*Attorney, Agent, or Firm*—Arnold S. Milowsky

[57] ABSTRACT

This invention provides a method of prophylactically preventing the onset, preventing the development, and arresting the progression of insulin dependent diabetes mellitus in a mammal by administering an effective amount of rapamycin either alone or in combination with insulin.

6 Claims, No Drawings

METHOD OF TREATING DIABETES

CROSS REFERENCE TO RELATED APPLICATION

This application is a continuation-in-part of Ser. No. 07/679,706, filed Apr. 3, 1991 and now abandoned.

BACKGROUND OF THE INVENTION

Insulin dependent diabetes mellitus (IDDM), a disease state occurring in 0.3% of the general population, is associated with insufficient insulin production causing metabolic changes such as hyperglycemia, glycosuria and decreased hepatic glycogen levels. Clinically, the disease is first observed as causing ravenous hunger, frequent urination and unquenchable thirst. Even with exogenously supplied insulin treatment, complications such as retinopathy, neuropathy, peripheral vascular disease, atherosclerosis, weight loss, stroke, renal failure, and coma leading to death occur.

The etiology of IDDM is attributed to an autoimmune response to the $\beta$-islet cells. The pancreatic islets become infiltrated with lymphocytes (insulitis) and the insulin-producing $\beta$-cells are destroyed. Approximately 80% of the $\beta$-cells are destroyed before clinically observable symptoms occur. Adoptive transfer studies in NOD mice [DV Serreze, Diabetes 37: 252 (1988)] have shown that T-cell mediated events occur initially in IDDM while humoral abnormalities (cytoplasmic islet cell, insulin, and 64 Kd protein autoantibodies) contribute later during the disease progression [M. A. Atkinson, Scientific Am. 62 (1990)]. Genetic susceptibility involving class II major histocompatability complex (MHC) appears to play a major role in this autoimmune disease. Approximately 60–70% of this susceptibility resides in the HLA region. [A. C. Tarn, Lancet 845 (1988)]. More than 95% of those individuals with IDDM are HLA DR3 and/or DR4 positive, whereas DR2 is negatively associated with the disease. [K. Wilson, Ann. Rev. Med. 41: 497 (1990)].

As treatment of IDDM with supplemental insulin is not completely satisfactory, current research has focused on developing agents for the treatment and prevention of IDDM. Several animal models have been utilized to study the etiology of IDDM and to evaluate potential forms of treatment and prevention.

Two standard animal models have been developed that emulate human IDDM. The first standard animal model, developed by Tochino [Exerpta Medica, 295 (1982)], the non-obese diabetic (NOD) mouse, is a mouse strain that spontaneously develops IDDM. Insulitis is initially observed at about 30 days of age, and by 140 days of age, approximately 70% of the female NOD mice develop IDDM. Marked mononuclear cell infiltration surrounding and/or invading Langerhans' islets with concomitant $\beta$-cell destruction are also observed. [Y. Mori, Diabetalogia 29: 244 (1986)]. The second standard animal model is the Bio Breeding (BB) rat, which develops gross abnormalities of the immune response including a T-cell lymphopenia preceding and accompanying the onset of IDDM. [C. R. Stiller, Science 223: 1362 (1984)].

The immunosuppressants cyclosporin A (CsA) and FK-506 have been evaluated in the BB rat and NOD mouse models of IDDM, and CsA has been evaluated in human clinical trials. CsA has been shown to be effective in prophylactically preventing the onset of IDDM and insulitis in both the NOD mouse and BB rat standard animal models, but was only partially effective in ameliorating IDDM when first administered after the onset of the initial symptoms of IDDM. [B. Formby, J. Pharm. Exp. Ther. 241: 106 (1987); C. R. Stiller, Metabolism 32 Supp 1: 69 (1983); and M. A. Jaworski, Clin. Invest. Med. 10: 488 (1987)]. One study reported that CsA had little therapeutic effect on IDDM in the NOD mouse standard animal model after the onset of IDDM. [Y. Mori, Diabetologia 29: 244 (1986)].

CsA has been evaluated in several clinical studies in newly diagnosed IDDM patients. CsA treatment was shown to reduce the dosage requirement of exogenously administered insulin and induced remission (non-insulin dependence) in about 23 to 50% of patients in these studies for up to 1 year. The percent of remission was highest in patients who started CsA treatment the earliest after IDDM diagnosis. Data on the longevity of remission following cessation of CsA treatment is inconclusive. One study reported remissions lasting for more than 9 months, whereas several other studies reported that remission was not maintained following discontinuation of CsA treatment. [G. Feutren, Lancet 119: (1986); J. Dupre, Diabetes 37: 1574, (1988); C. R. Stiller, Science 223: 1362 (1984); R. Lipton, Diabetes Care, 13: 776 (1990); K. Wilson, Annu. Rev. Med. 41: 497 (1990)].

FK-506 has been demonstrated to prevent the onset of IDDM in both the NOD and BB standard animal models of IDDM. Two studies have shown that FK-506 induced prevention of IDDM lasted 45 days and 20 weeks, respectively, beyond termination of FK-506 treatment in about 75% of animals that had not developed IDDM when FK-506 treatment was discontinued. [N. Murase, Diabetes 39: 1584 (1990); K. Kurasawa, Clin. Immun. Immunopath. 57: 274 (1990); J. Miyagawa, Diabetologia 33: 503 (1990)].

Rapamycin, a macrocyclic triene antibiotic produced by *Streptomyces hygroscopicus* [U.S. Pat. No. 3,929,992] has been shown to prevent the formation of humoral (IgE-like) antibodies in response to an albumin allergic challenge [Martel, R., Can. J. Physiol. Pharm. 55: 48 (1977)], inhibit murine T-cell activation [Staruch, M., FASEB 3: 3411 (1989)], and prolong survival time of organ grafts in histoincompatible rodents [Morris, R., Med. Sci. Res. 17: 877 (1989)].

DESCRIPTION OF THE INVENTION

This invention provides a method for arresting the development or retarding the progression of IDDM in a mammal in need thereof by administering an effective amount of rapamycin orally, parenterally, intranasally, intrabronchially, or rectally. This invention also provides a method of prophylactically preventing the onset of insulin dependent diabetes mellitus in an insulin dependent diabetes mellitus susceptible mammal which comprises, administering a prophylactically effective amount of rapamycin to said mammal. When rapamycin is used for arresting the development or retarding the progression of IDDM, it is preferable that rapamycin be administered in combination with insulin.

The effect of rapamycin on IDDM was established in the NOD mouse. Diabetes in the NOD mouse has the following similarities with human IDDM: 1) diabetes is genetically linked with loci within the major histocompatability region; 2) infiltration of the pancreatic islets with lymphocytes (insulitis) is associated with selective destruction of the insulin-secreting $\beta$-cells; and 3) autoantibodies to islet surface antigens are detectable in blood. [M. Fagan, Diabetes 40: 715 (1991)]. The NOD mouse model also has been described as being valuable not only for elucidation of the pathogenisis of type I IDDM in man, but in designing and testing effective therapies for prevention of IDDM. [E. Leiter, Am. J. Path. 128: 380 (1987)]. The NOD mouse is therefore considered to be the standard animal model emulating IDDM in humans.

The procedures used and results obtained are described below. CsA also was evaluated in the NOD mouse, under identical conditions, for the purpose of comparison.

Female NOD mice were housed in a barrier facility and fed food and water ad libitum. Rapamycin was evaluated in a series of two test procedures that evaluated different dose ranges. In the first study, mice were randomly divided into four treatment groups: naive control, CsA (12 mg/kg), rapamycin (6 mg/kg), and rapamycin (12 mg/kg). Treatment groups contained either 6 or 7 mice per group. In the second study, mice were randomly divided into five treatment groups: naive control, vehicle control, rapamycin (6 mg/kg), rapamycin (0.6 mg/kg), and rapamycin (0.06 mg/kg). Treatment groups in the second study contained 10 mice per group. Both immunosuppressants were dissolved in vehicle containing 8% cremophor EL and 2% ethanol. In the first study, administration of drug began at 56 days of age and continued 3 times per week orally until the mice reached 170 days of age. In the second study, administration of drug began at 64 days of age and continued 3 times per week orally until the mice reached 176 days of age. Weight and water consumption were measured on a weekly basis. Blood was collected at regular intervals and blood plasma glucose levels were measured enzymatically. Plasma levels of $\beta$-hydroxybutyrate, triglyceride, and cholesterol were evaluated following the end of treatment in the second. The incidence of IDDM following the cessation of treatment with rapamycin was also evaluated in the second study.

The following table shows the mean plasma glucose levels for the mice in each treatment group in the first study. Plasma levels are expressed in mg/dL.

| MEAN PLASMA GLUCOSE LEVELS (mg/dL $\pm$ SE) - STUDY 1 | | | | |
| --- | --- | --- | --- | --- |
| | Treatment Group | | | |
| Age of Mice | Naive | Rapamycin (6 mg/kg) | Rapamycin (12 mg/kg) | CsA (12 mg/kg) |
| 56 days | 130 $\pm$ 5 | 113 $\pm$ 3 | 114 $\pm$ 3 | 126 $\pm$ 2 |
| 66 days | 102 $\pm$ 4 | 128 $\pm$ 6 | 116 $\pm$ 10 | 106 $\pm$ 9 |
| 73 days | 119 $\pm$ 8 | 147 $\pm$ 14 | 128 $\pm$ 5 | 127 $\pm$ 6 |
| 85 days | 128 $\pm$ 8 | 138 $\pm$ 4 | 145 $\pm$ 14 | 128 $\pm$ 5 |
| 94 days | 128 $\pm$ 4 | 155 $\pm$ 8 | 143 $\pm$ 15 | 137 $\pm$ 4 |
| 108 days | 17 $\pm$ 10 | 132 $\pm$ 2 | 122 $\pm$ 6 | 130 $\pm$ 8 |
| 129 days | 398 $\pm$ 133 | 150 $\pm$ 7 | 141 $\pm$ 4 | 357 $\pm$ 0 |
| 143 days | 660 $\pm$ 101 | 133 $\pm$ 6 | 137 $\pm$ 9 | 404 $\pm$ 72 |
| 157 days | 483 $\pm$ 122 | 137 $\pm$ 6 | 129 $\pm$ 11 | 570 $\pm$ 75 |
| 171 days | 475 $\pm$ 69 | 151 $\pm$ 7 | 1147 $\pm$ 7 | 562 $\pm$ 52 |

Results obtained in the second study are shown below.

| MEAN PLASMA GLUCOSE LEVELS (mg/dL $\pm$ SE) - STUDY 2 | | | | | |
| --- | --- | --- | --- | --- | --- |
| | Treatment Group | | | | |
| Age of Mice | Naive | Vehicle | Rapamycin (6 mg/kg) | Rapamycin (0.6 mg/kg) | Rapamycin (0.06 mg/kg) |
| 79 days | 124 $\pm$ 3.7 | 138 $\pm$ 6.6 | 151 $\pm$ 4.5 | 139 $\pm$ 3.2 | 129 $\pm$ 3.3 |
| 107 days | 420 $\pm$ 192 | 388 $\pm$ 109 | 124 $\pm$ 3.0 | 130 $\pm$ 6.2 | 430 $\pm$ 113 |
| 135 days | 603 $\pm$ 46 | 595 $\pm$ 17 | 156 $\pm$ 7.4 | 139 $\pm$ 5.3* | 598 $\pm$ 44 |
| 176 days | 766 $\pm$ 76 | 769 $\pm$ 139 | 161 $\pm$ 15 | 142 $\pm$ 19 | 718 $\pm$ 99 |

*One of ten mice became diabetic (678 mg/dL) and expired at 166 days of age. This value was not included in the group mean.

A plasma glucose level consistently above 200 mg/dL was the criterion used to determine overt onset of IDDM. With the exception of 1 mouse in the 0.6 mg/kg group, plasma glucose levels for mice treated with rapamycin at oral doses of 12, 6, and 0.6 mg/kg remained below 200 mg/dL throughout the entire treatment period demonstrating that rapamycin prevented the onset of IDDM. As expected, the untreated NOD mice (naive) developed IDDM by 129 days in study 1 and by 107 days in study 2 for both naive and vehicle-treated NOD mice. There was no difference observed between naive and vehicle-treated NOD mice. These results also indicate that CsA, under these conditions, was ineffective in preventing the onset of IDDM; mean plasma glucose levels were above 200 mg/dL by 129 days. Rapamycin given orally at 0.06 mg/kg also was ineffective at preventing the onset of IDDM.

The following table shows the percent of mice in each treatment group that developed IDDM. Plasma glucose levels consistently above 200 mg/dL were considered to be determinative of the onset of IDDM.

| PERCENT OF MICE THAT DEVELOPED IDDM - STUDY 1 | | | | |
| --- | --- | --- | --- | --- |
| | Treatment Group | | | |
| Age of Mice | Naive | Rapamycin (6 mg/kg) | Rapamycin (12 mg/kg) | CsA (12 mg/kg) |
| 129 days | 33% | 0% | 0% | 14% |
| 143 days | 33% | 0% | 0% | 43% |
| 157 days | 67% | 0% | 0% | 57% |
| 171 days | 67% | 0% | 0% | 71% |

The following table shows the results obtained in the second study.

| PERCENT OF MICE THAT DEVELOPED IDDM - STUDY 2 | | | | | |
|---|---|---|---|---|---|
| | Treatment Group | | | | |
| Age of Mice | Naive | Vehicle | Rapamycin (6 mg/kg) | Rapamycin (0.6 mg/kg) | Rapamycin (0.06 mg/kg) |
| 79 days | 0% | 0% | 0% | 0% | 0% |
| 107 days | 20% | 30% | 0% | 0% | 30% |
| 135 days | 50% | 50% | 0% | 10% | 60% |
| 176 days | 60% | 60% | 0% | 10% | 60% |

In the first study, the onset of IDDM was observed by 129 days in mice that were either untreated or treated with CsA. By 171 days 67% of untreated mice and 71% of mice treated with CsA had developed IDDM. In the first study, rapamycin, at oral doses of 6 and 12 mg/kg, significantly (p=0.008, Fisher's exact test) prevented the onset of IDDM as compared with the control group. No rapamycin-treated mice (6 mg/kg and 12 mg/kg) developed IDDM. In the second study, rapamycin, at oral doses of 0.6 and 6 mg/kg, prevented the onset of IDDM in 10 of 10 and 9 of 10 mice evaluated, respectively. The incidence of IDDM in the rapamycin treated NOD mice in the second study was significantly lower (p=0.029 for 0.6 mg/kg rapamycin and p=0.005 for 6 mg/kg rapamycin) than observed for the naive or vehicle-treated NOD mice. There were no significant differences between the incidence of IDDM in naive mice and in the vehicle-treated mice. These results demonstrate that rapamycin effectively prevented the development of IDDM at oral doses of 12, 6, and 0.6 mg/kg.

A progressive increase in water consumption is observed with the onset of IDDM both in the NOD mouse and humans. The following table shows the mean water consumption for the NOD mice in each treatment group.

| MEAN WATER CONSUMPTION (mL/day ± SE) - STUDY 1 | | | | |
|---|---|---|---|---|
| | Treatment Group | | | |
| Age of Mice | Naive | Rapamycin (6 mg/kg) | Rapamycin (12 mg/kg) | CsA (12 mg/kg) |
| 60 days | 4.3 ± 0.04 | 3.4 ± 0.4 | 4.0 ± 0 | 4.6 ± 0.1 |
| 74 days | 5.0 ± 0.02 | 4.5 ± 0.1 | 4.5 ± 0.1 | 4.3 ± 0.04 |
| 88 days | 5.2 ± 0.02 | 5.0 ± 0.1 | 5.6 ± 0.3 | 4.5 ± 0.1 |
| 102 days | 5.1 ± 0.1 | 4.3 ± 0.2 | 5.6 ± 0.1 | 4.0 ± 0.2 |
| 116 days | 5.5 ± 0.2 | 4.6 ± 0.2 | 6.6 ± 0.3 | 4.2 ± 0.2 |
| 130 days | 8.8 ± 1.7 | 5.1 ± 0.1 | 6.6 ± 0.2 | 4.7 ± 0.2 |
| 144 days | 17.2 ± 5.5 | 5.2 ± 0.2 | 6.5 ± 0.5 | 9.5 ± 0.5 |
| 158 days | 16.7 ± 4.9 | 4.5 ± 0.1 | 5.8 ± 0.8 | 18.3 ± 0.4 |
| 172 days | 19.6 ± 3.3 | 4.8 ± 0.1 | 6.9 ± 0.6 | 24.5 ± 0.2 |

The following results were obtained in the second study.

| MEAN WATER CONSUMPTION (mL/day ± Se) - STUDY 2 | | | | | |
|---|---|---|---|---|---|
| | Treatment Group | | | | |
| Age of Mice | Naive | Vehicle | Rapamycin (6 mg/kg) | Rapamycin (0.6 mg/kg) | Rapamycin (0.06 mg/kg) |
| 75 days | 4.4 ± 0 | 4.4 ± 0.1 | 4.9 ± 0 | 4.4 ± 0.1 | 4.8 ± 0.1 |
| 89 days | 4.5 ± 0.1 | 4.0 ± 0 | 4.2 ± 0.1 | 4.0 ± 0.1 | 4.2 ± 0 |
| 103 days | 7.1 ± 1.2 | 6.3 ± 0.9 | 4.4 ± 0.1 | 4.2 ± 0.1 | 6.9 ± 0.8 |
| 117 days | 7.5 ± 1.2 | 8.5 ± 1.5 | 4.7 ± 0.1 | 5.2 ± 0.2 | 10.2 ± 1.6 |
| 131 days | 10.5 ± 1.2 | 14.0 ± 1.6 | 4.7 ± 0 | 5.8 ± 0.8 | 17.0 ± 3.6 |
| 145 days | 16.3 ± 2.2 | 22.9 ± 2.2 | 4.9 ± 0.1 | 8.8 ± 2.2* | 16.1 ± 1.3 |
| 159 days | 17.2 ± 1.5 | 20.8 ± 2.4 | 4.8 ± 0.1 | 5.5 ± 0.6 | 21.3 ± 1.9 |
| 173 days | 20.1 ± 1.5 | 14.6 ± 2.9 | 4.7 ± 0.1 | 5.2 ± 0 | 15.4 ± 2.3 |

*One of ten mice became diabetic (678 mg/dL) and expired at 166 days of age. This value was included in the group mean and accounts for the elevated mean water consumption observed at 145 days.

These results show that rapamycin, at oral doses of 12, 6, and 0.6 mg/kg prevented the progressive increase in water consumption that is associated with the onset of IDDM; water consumption increased only slightly over time concomitant with normal weight gain in the mice. The water consumption of the untreated NOD mice increased as expected with the onset of IDDM. Mice treated with CsA consumed water in approximately the same quantities as untreated mice, indicating that CsA, under these conditions, did not prevent the onset of IDDM.

In the second study, treatment was initiated when the mice were 64 days of age. Following the cessation of treatment in the second study when the mice were 176 days of age, plasma levels of β-hydroxybutyrate, triglycerides, and cholesterol were measured. In NOD mice that developed IDDM, levels of β-hydroxybutyrate, triglycerides, and cholesterol were significantly elevated compared with vehicle control nondiabetic mice. A similar elevation of β-hydroxybutyrate, triglycerides, and cholesterol levels is observed in humans with IDDM. Treatment with rapamycin at either 0.6 or 6 mg/kg orally, prevented the elevation of levels of β-hydroxybutyrate, triglycerides, and cholesterol that are associated with the onset and progression of IDDM, further confirming the ability to prevent the onset of IDDM in the NOD mouse.

Following the cessation of treatment with rapamycin in the second study, the mice that had not developed IDDM during the study (100% NOD mice at 6 mg/kg and 90% NOD mice at 0.6 mg/kg rapamycin, respectively) were evaluated for an additional 41 weeks to further establish the protective effect of rapamycin. The following table shows the incidence of IDDM following the cessation of rapamycin in NOD mice that had not developed IDDM during treatment with rapamycin. The onset of IDDM was determined by plasma glucose levels and other clinical signs of IDDM including weight loss and increased water consumption.

| INCIDENCE OF IDDM AFTER CESSATION OF TREATMENT - STUDY 2* | | |
|---|---|---|
| Number of Weeks After Cessation | Rapamycin (6 mg/kg) Percent of IDDM | Rapamycin (0.6 mg/kg) Percent of IDDM |
| 1 | 0% | 0% |
| 3 | 0% | 0% |
| 6 | 0% | 11% |
| 9 | 0% | 11% |
| 15 | 0% | 11% |
| 21 | 0% | 22% |
| 26 | 0% | 22% |
| 33 | 0% | 33% |
| 37 | 0% | 33% |
| 41 | 0% | 33% |

*The mice evaluated in this portion of the study included the 10 mice treated with 6 mg/kg rapamycin that did not develop IDDM during the treatment period and the 9 mice treated with 0.6 mg/kg rapamycin that did no develop IDDM during the treatment period.

These results show that not only did rapamycin prevent the onset of IDDM during the treatment period, but treatment with rapamycin either reduced expected levels of disease incidence or prevented the onset of IDDM after treatment had ceased indicating that initial treatment with rapamycin preserved β-cell function even after treatment was stopped. These data further confirm the ability of rapamycin to prophylactically prevent the onset of IDDM. Additionally, these data suggest that continuous long-term treatment may not be necessary, possibly allowing for an intermittent dosing regimen of rapamycin to prevent the onset, arrest the progression, or retard the progression of IDDM.

The results of this in vivo standard pharmacological test procedure emulating IDDM in humans demonstrates that rapamycin effectively prevented the overt onset of IDDM and is therefore useful in prophylactically preventing the onset, arresting the development, or retarding the progression of IDDM.

Rapamycin (6 mg/kg) was also administered intermittently to NOD mice that had already developed IDDM (130–144 days of age), and was unable to reverse the course of the disease. It is possible that rapamycin could not reverse the course of IDDM because the intermittent dosing schedule may not have raised rapamycin blood levels to a therapeutic range soon enough to abrogate attack by T-lymphocytes on the remaining pancreatic β-cells. Higher blood levels of rapamycin are obtained when rapamycin is administered parenterally. Following the onset of IDDM, rapamycin should be administered in sufficient dosage (preferably via parenteral administration), and preferably in combination with insulin to arrest the development and retard the progression of IDDM, while preserving any β-cells that have not yet been destroyed. Combination therapy in a clinical trial using CsA and insulin initiated soon after diagnosis of IDDM increased the rate of remission of IDDM and enhanced β-cell function during the first year of IDDM. [C. R. Stiller, Diabetes 37: 1574 (1988)].

As such rapamycin will be generally useful in treating at least two classes of human patients. The first group are those who have already developed clinically observable signs of IDDM. As seen in clinical studies with CsA, it is preferable to start treatment with rapamycin at the earliest point after diagnosis, to spare remaining β-cells from being destroyed. [J. Dupre, Diabetes 37: 1574, (1988); C. R. Stiller, Science 223: 1362 (1984)]. In this patient population, it is preferable that rapamycin be administered in combination with insulin. In addition to aiding the maintenance of normal glucose tolerance, concomitant insulin administration is also believed to reduce the burden on the remaining β-cells, thus having a sparing effect on them.

A second group of patients, are those who have not yet developed clinically observable symptoms of IDDM, but are predisposed to developing IDDM, either based on subclinical development of IDDM or because of genetic predisposition. Clinically observable IDDM does not develop suddenly, but progresses silently for several years, as the immune system slowly eliminates the β-cells. [M. A. Atkinson, Sci. Am. 60, July 1990]. While the classic symptoms of IDDM appear only when at least 80% of the β-cells have been destroyed, it has now become more predictable to determine which individuals will develop IDDM long before clinical symptoms are manifested. The onset of IDDM has become increasingly predictable through the detection of its associated autoantibodies and other selective markers. The predictability applies both to the low risk general population, as well as relatives who are at higher risk. [N. Maclaren, Diabetes 37: 1591 (1988)]. These autoantibodies and markers include cytoplasmic islet cell autoantibodies (ICA), insulin autoantibodies (IAA), auto antibodies to a 64K protein, and diminished first-phase insulin in response to an intravenous glucose load (IVGTT). Both ICA and IAA have been observed in humans decades before they developed IDDM. [K. Wilson, Ann. Rev. Med. 41: 497 (1990)]. It has been shown that individuals with ICA have a 42% risk of developing IDDM, whereas those without ICA have a 0.6% risk of developing IDDM. Analysis of ICA-subfractions further refined this predictability. Life table analysis projects that 78% of individuals that test positive for complement-fixing ICA will develop IDDM, whereas only 3% of those individuals with non-complement-fixing ICA will develop IDDM. [A. C. Tarn, Lancet 845 (1988)]. Additionally, it is believed that virtually 100% of children and young adults will develop autoantibodies to the 64K β-cell membrane protein before the onset of IDDM. [N. Maclaren, Diabetes 37: 1591 (1988)].

Other susceptible individuals include first degree relatives of individuals with IDDM (5% risk of developing IDDM) and identical twins of an individual with IDDM (50% risk of developing IDDM). Both of these categories are substantially at greater risk of developing IDDM than the general population is (0.3% risk of developing IDDM). [K. Wilson, Ann. Rev. Med. 41: 497 (1990)].

For the prophylaxis of IDDM in susceptible individuals, rapamycin may be administered as the sole active ingredient or in combination with insulin. The administration of insulin prophylactically has been reported to reduce the incidence of development of IDDM in NOD mice. [M. A. Atkinson, Diabetes 39: 933 (1990).]

Other groups of susceptible individuals to whom rapamycin may be given prophylactically will be apparent to one skilled in the art.

When rapamycin is employed in the treatment of IDDM, it can be formulated into oral dosage forms such as tablets, capsules and the like. Rapamycin can be administered alone or by combining it with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. Rapamycin may be encapsulated with or without other carriers. In all cases, the proportion of active ingredients in said compositions both solid and liquid will be at least to impart the desired activity thereto on oral administration. Rapamycin may also be injected parenterally, in which case it is used in the form of a sterile solution containing other solutes, for example, enough saline or glucose to make the solution isotonic. For administration by intranasal or intrabronchial inhalation or insufflation, rapamycin may be formulated into an aqueous or partially aqueous solution, which can then be utilized in the form of an aerosol.

Rapamycin can also be combined with insulin and preferably be administered parenterally, in which case it is used in the form of a sterile solution containing other solutes, for example, enough saline or glucose to make the solution isotonic.

The dosage requirements vary with the particular compositions employed, the route of administration, the severity of the symptoms presented and the particular subject being treated. Based on the results obtained in the standard pharmacological test procedure, projected oral daily dosages of rapamycin to maintain normal glucose levels would be 0.1-25 mg/kg, preferably between 0.5-18 mg/kg, and more preferably between 0.5-12 mg/kg. When rapamycin is administered parenterally, it is expected that the minimal dosage requirement will be about ten times less. Therefore, projected parenteral daily dosages of rapamycin to maintain normal glucose levels would be 0.01-25 mg/kg, preferably between 0.05-18 mg/kg, and more preferably between 0.05-12 mg/kg.

When rapamycin is administered in combination with insulin, the dose of insulin may either be the same as is needed without rapamycin treatment or may be reduced to below the amount that would otherwise be needed to maintain normal glucose levels. Self determined capillary blood glucose levels can be easily measured, and doses of insulin can be administered to the extent necessary to maintain acceptable blood glucose levels. Rapamycin and insulin need not be administered simultaneously. For example, rapamycin may be administered once per day, several times per day, or several times per week, while insulin may only need to be administered once per day. The dosage schedule will vary depending on the individual needs of the patient. The same dosage ranges for rapamycin are applicable when rapamycin is administered in combination with insulin.

Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. An effective dose will generally be the dose at which normal glucose levels are maintained. In general, rapamycin is most desirably administered at a concentration that will generally afford effective results without causing any harmful or deleterious side effects, and can be administered either as a single unit dose, or if desired, the dosage may be divided into convenient subunits administered at suitable times throughout the day or week, depending on the patient.

What is claimed is:

1. A method for arresting the development or retarding the progression of insulin dependent diabetes mellitus in a mammal in need thereof which comprises administering an effective amount of rapamycin orally, parenterally, intranasally, intrabronchially, or rectally to said mammal.

2. The method according to claim 1 which further comprises administering the rapamycin in combination with insulin wherein the insulin is administered parenterally.

3. The method according to claim 2 wherein the amount of insulin needed to maintain normal glucose levels is less than would otherwise be needed to maintain normal glucose levels by the administration of insulin alone.

4. A composition comprising rapamycin, insulin, and a pharmaceutically acceptable carrier for the use in arresting the development or retarding the progression of insulin dependent diabetes mellitus in a mammal in need thereof.

5. The composition of claim 4 wherein the amount of insulin needed to maintain normal glucose levels is less than would otherwise be needed to maintain normal glucose levels by the administration of insulin alone.

6. A method preventing the onset of insulin dependent diabetes mellitus in an insulin dependent diabetes mellitus susceptible mammal which comprises, administering a prophylactically effective amount of rapamycin to said mammal.

* * * * *